United States Patent
Suzuki et al.

(10) Patent No.: US 11,123,683 B2
(45) Date of Patent: Sep. 21, 2021

(54) CARBON DIOXIDE ABSORBENT AND APPARATUS OF SEPARATING AND RECOVERING CARBON DIOXIDE

(71) Applicant: Kabushiki Kaisha Toshiba, Minato-ku (JP)

(72) Inventors: Akiko Suzuki, Ota (JP); Asato Kondo, Yokohama (JP); Takashi Kuboki, Ota (JP); Shinji Murai, Sagamihara (JP); Mitsuru Udatsu, Kawasaki (JP); Toshihiro Imada, Kawasaki (JP); Yoshihiko Nakano, Yokohama (JP); Reiko Yoshimura, Kawasaki (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 0 days.

(21) Appl. No.: 15/903,613

(22) Filed: Feb. 23, 2018

(65) Prior Publication Data
US 2019/0083921 A1    Mar. 21, 2019

(30) Foreign Application Priority Data

Sep. 21, 2017 (JP) ............................. JP2017-181749

(51) Int. Cl.
*C07D 241/04* (2006.01)
*B01D 53/14* (2006.01)
*B01D 53/96* (2006.01)

(52) U.S. Cl.
CPC ......... *B01D 53/1475* (2013.01); *B01D 53/96* (2013.01); *C07D 241/04* (2013.01);
(Continued)

(58) Field of Classification Search
None
See application file for complete search history.

(56) References Cited

U.S. PATENT DOCUMENTS 4,421,905 A * 12/1983 Lee .................. C08G 18/346
                                              528/52
4,446,119 A    5/1984 Dupart et al.
(Continued)

FOREIGN PATENT DOCUMENTS

CN    102284227 A    12/2011
CN    102284229 A    12/2011
(Continued)

OTHER PUBLICATIONS

Khalili, F. et al. "$pK_a$ Values of Some Piperazines at (298, 303, 313, and 323) K" Journal of Chemical and Engineering Data, American Chemical Society, vol. 54, No. 10, 2009, pp. 2914-2917.
(Continued)

*Primary Examiner* — Daniel Berns
(74) *Attorney, Agent, or Firm* — Oblon, McClelland, Maier & Neustadt, L.L.P.

(57) ABSTRACT

A carbon dioxide absorbent of an embodiment includes a heterocyclic amine expressed by Formula (1), and the heterocyclic amine having a pKa of any one amino group included in a heterocyclic ring in Formula (1) in a range of 7.0 or more to 8.6 or less and an organic solvent having a boiling point of 150° C. or more at 1 atm. A total mass of the heterocyclic amine and the organic solvent is 70 mass % or more to 100 mass % or less of the carbon dioxide absorbent. Each of $R^1$ to $R^4$ in Formula (1) is H, oxygen double-bonded with carbon of the heterocyclic ring, $CH_3$, OH, or an alkyl chain optionally including a functional group. $X^1$ in Formula (1) is H, $CH_3$, CO, $C(O)OC_2H_5$, $C(O)OC_3H_7$, $C(O)OCH(CH_3)_2$, $C(O)OC(CH_3)_3$, $C(O)OCH_3$, $C(O)CH_3$, or $C(O)C_2H_5$.

16 Claims, 2 Drawing Sheets

Formula (1)

Formula (2)

Formula (3)

Formula (4)

(52) U.S. Cl.
CPC ............... B01D 2252/202 (2013.01); B01D 2252/20447 (2013.01); B01D 2257/504 (2013.01)

(56) References Cited

U.S. PATENT DOCUMENTS

| | | | |
|---|---|---|---|
| 4,483,833 A | 11/1984 | Stogryn et al. | |
| 5,098,681 A | 3/1992 | Christiansen et al. | |
| 5,433,934 A | 7/1995 | Chang et al. | |
| 5,622,681 A | 4/1997 | Grierson et al. | |
| 6,110,922 A * | 8/2000 | Link | C07D 211/60 514/266.3 |
| 6,271,234 B1 * | 8/2001 | Leonardi | C07D 213/75 514/253.01 |
| 6,423,282 B1 | 7/2002 | Araki et al. | |
| 7,718,151 B1 | 5/2010 | Hu | |
| 2006/0104877 A1 | 5/2006 | Cadours et al. | |
| 2009/0199709 A1 | 8/2009 | Rojey et al. | |
| 2012/0161071 A1 | 6/2012 | Murai et al. | |
| 2012/0308451 A1 | 12/2012 | Murai et al. | |
| 2013/0309155 A1 | 11/2013 | Parisi | |
| 2014/0301927 A1 | 10/2014 | Udatsu et al. | |
| 2017/0072361 A1 | 3/2017 | Yoon et al. | |
| 2017/0266607 A1 | 9/2017 | Watando et al. | |
| 2018/0001255 A1 | 1/2018 | Bumb et al. | |

FOREIGN PATENT DOCUMENTS

| | | |
|---|---|---|
| CN | 106390690 | 2/2017 |
| EP | 0 270 223 A1 | 6/1988 |
| JP | 6-502349 | 3/1994 |
| JP | 3210365 | 9/2001 |
| JP | 3322405 | 9/2002 |
| JP | 2006-136885 | 6/2006 |
| JP | 2008-168184 | 7/2008 |
| JP | 2009-529420 | 8/2009 |
| JP | 2010-155753 | 7/2010 |
| JP | 2012-143744 | 8/2012 |
| JP | 2012-143745 | 8/2012 |
| JP | 2012-245483 | 12/2012 |
| JP | 2013-13854 A | 1/2013 |
| JP | 2015-54279 A | 3/2015 |
| JP | 2015-199007 | 11/2015 |
| JP | 2017-35669 | 2/2017 |
| JP | 2017-121610 | 7/2017 |
| JP | 2017-164696 | 9/2017 |
| WO | WO 2012/162944 A1 | 12/2012 |
| WO | WO 2016/116815 A1 | 7/2016 |

OTHER PUBLICATIONS

Closmann, F. et al. "MDEA/Piperazine as a solvent for $CO_2$ capture" Energy Procedia 1, ScienceDirect, 2009, pp. 1351-1357.

Herová, D. "Direct $N^1$-Monosubstitutions of Piperazine and Applications of Their Products in Syntheses" Masaryk University, 2015, 226 pages.

Freeman, S.A. et al, "Piperazine/N-methylpiperazine/N,N'-dimethylpiperazine as an Aqueous Solvent for Carbon Dioxide Capture" Oil and Gas Science and Technology, vol. 69, No. 5, 2014, pp. 903-914 and Cover Page.

Li, H. et al. "Characterization of Piperazine/2-Aminomethylpropanol for Carbon Dioxide Capture" Energy Procedia 37, SciVerse ScienceDirect, 2013, pp. 340-352.

* cited by examiner

Formula (1)

Formula (2)

Formula (3)

Formula (4)

US 11,123,683 B2

CARBON DIOXIDE ABSORBENT AND APPARATUS OF SEPARATING AND RECOVERING CARBON DIOXIDE

CROSS-REFERENCE TO RELATED APPLICATION

This application is based upon and claims the benefit of priority from Japanese Patent Application No. 2017-181749, filed on Sep. 21, 2017; the entire contents of which are incorporated herein by reference.

FIELD

Embodiments described herein relate to carbon dioxide absorbent and an apparatus of separating and recovering carbon dioxide.

BACKGROUND

On the basis of a recent concern for global warming and strengthening of regulations, reduction of carbon dioxide emission from coal-fired power plants has been an urgent task. Therefore, as a method of reducing carbon dioxide emission, recovery of carbon dioxide by a chemical absorbent in addition to reduction of carbon dioxide emission by increasing efficiency of power plants is receiving great attention. As a specific absorbent, absorption by amines has been studied from the past. It is known that amine contained in a composition is dispersed by heating of a chemical absorption solution in a process of absorbing and emitting carbon dioxide using the chemical absorbent. Since there is a concern about an influence on a surrounding environment of a plant when a large amount of amine is dispersed in the air, an amine trap by water, an acid, or the like is installed.

DETAILED DESCRIPTION

Figure 1:
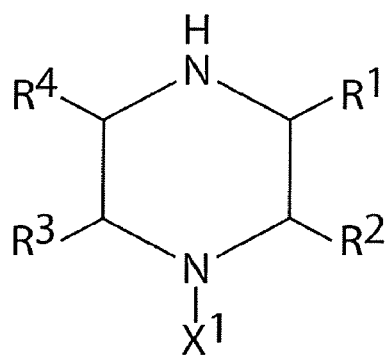
FIG. 1 shows structural formulas included in a carbon dioxide absorbent according to embodiments.
Figure 1:
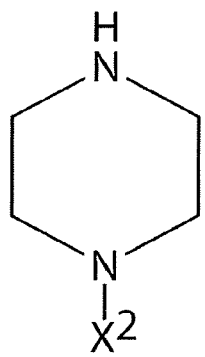
Figure 1:
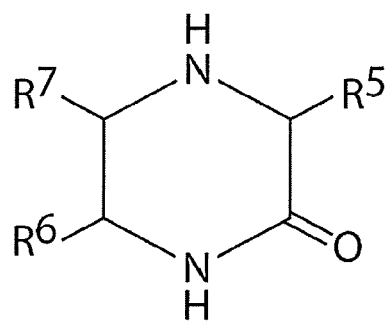
Figure 1:
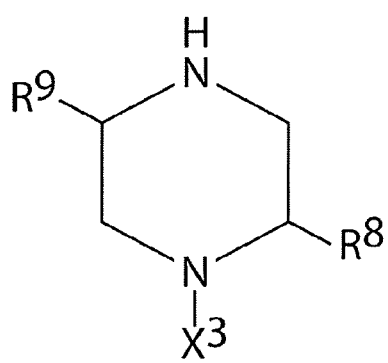

A carbon dioxide absorbent of embodiments includes a heterocyclic amine expressed by Formula (1), and the heterocyclic amine having a pKa of anyone amino group included in a heterocyclic ring in Formula (1) in a range of 7.0 or more to 8.6 or less and an organic solvent having a boiling point of 150° C. or more at 1 atm. A total mass of the heterocyclic amine and the organic solvent is 70 mass % or more to 100 mass % or less of the carbon dioxide absorbent. Each of $R^1$ to $R^4$ in Formula (1) is H, oxygen double-bonded with carbon of the heterocyclic ring, $CH_3$, OH, or an alkyl chain optionally including a functional group. $X^1$ in Formula (1) is H, $CH_3$, CO, $C(O)OC_2H_5$, $C(O)OC_3H_7$, $C(O)OCH(CH_3)_2$, $C(O)OC(CH_3)_3$, $C(O)OCH_3$, $C(O)CH_3$, or $C(O)C_2H_5$.

A carbon dioxide absorbent according to embodiments includes a heterocyclic amine and an organic solvent. The heterocyclic amine according to embodiments is illustrated in Formula (1) of FIG. 1.

In the heterocyclic amine according to embodiments, it is practical that pKa of any one of the amino groups included in a heterocyclic ring of Formula (1) is 7.0 or more to 8.6 or less. Generally, heterocyclic amine has a pKa of about 9, where carbon dioxide hardly desorbs, and there is a need to raise a temperature in order to desorb carbon dioxide. It is possible to separate and recover carbon dioxide by absorption and desorption of carbon dioxide, but the largest amount of energy is required in a process of raising the temperature of the carbon dioxide absorbent at the time of desorption of carbon dioxide. The heterocyclic amine according to embodiments can reduce energy at the time of desorption of carbon dioxide. Further, since general heterocyclic amines have low solubility in organic solvents, a combination of a carbon dioxide absorbent containing a heterocyclic amine and an organic solvent as main components in a single phase state in which phase separation does not occur is not known.

The carbon dioxide absorbent according to embodiments may be used, for example, in an apparatus of separating and recovering carbon dioxide including: an absorption tower separating and recovering carbon dioxide from gas containing carbon dioxide by contacting the gas containing carbon dioxide with the carbon dioxide absorbent to allow carbon dioxide to be absorbed in the carbon dioxide absorbent; and a regeneration tower regenerating the carbon dioxide absorbent by desorbing carbon dioxide from the carbon dioxide absorbent which has absorbed carbon dioxide.

Each of $R^1$, $R^2$, $R^3$, and $R^4$ in Formula (1) is H, oxygen double-bonded with carbon of the heterocyclic ring, $CH_3$, OH, or an alkyl chain optionally having a functional group. Further, $X^2$ in Formula (1) is H, $CH_3$, CO, $C(O)OC_2H_5$, $C(O)OC_3H_7$, $C(O)OCH(CH_3)_2$, $C(O)OC(CH_3)_3$, $C(O)OCH_3$, $C(O)CH_3$, or $C(O)C_2H_5$. The alkyl chain optionally having a functional group may be, for example, a linear or branched alkyl chain having a hydroxyl group and 1 to 4 carbon atoms. Besides, examples of the functional group of the alkyl chain optionally having a functional group may include at least one selected from the group consisting of; an amino group, a carbonyl group, and a sulfo group.

More specific examples of the heterocyclic amine expressed by Formula (1) may include heterocyclic amines expressed by Formulas (2) to (4) of FIG. 1.

In the heterocyclic amine expressed by Formula (2), one amino group in a heterocyclic ring is bonded with a carbonyl aldehyde or carboxylic acid ester. $X^2$ of the heterocyclic amine expressed by Formula (2) is CO, $C(O)OC_2H_5$, $C(O)OC_3H_7$, $C(O)OCH(CH_3)_2$, $C(O)OC(CH_3)_3$, $C(O)OCH_3$, $C(O)CH_3$, or $C(O)C_2H_5$.

More specific examples of the heterocyclic amine expressed by Formula (2) may include at least one selected from the group consisting of; 1-piperazinecarbaldehyde, 1-ethoxycarbonylpiperazine, 1-n-propyloxycarbonylpiperazine, 1-i-propyloxycarbonylpiperazine, 1-piperazinecarboxylic acid-1-methylethyl ester, 1-Boc-piperazine, and the like. In these amines, a pKa of an amino group of the heterocyclic ring which is not bonded with the carbonyl aldehyde or carboxylic acid ester is 7.0 or more to 8.6 or less. 1-(1-piperazinyl)-2-propanone is similar to the heterocyclic amine expressed by Formula (2), but has a pKa of 9.1, and accordingly, 1-(1-piperazinyl)-2-propanone is not practical as the heterocyclic amine according to embodiments.

The heterocyclic amines expressed by Formulas (3) and (4) are piperazinones. $R^5$, $R^6$, and $R^7$ of the heterocyclic amine expressed by Formula (3) are all H. Alternatively, any one of $R^5$, $R^6$, and $R^7$ is $CH_3$ or $C_2H_5$, and the others are H. Further, $R^8$ of the heterocyclic amine expressed by Formula (4) is oxygen double-bonded with carbon of the heterocyclic ring and $R^9$ is H; or $R^8$ is H and $R^9$ is oxygen double-bonded with carbon of the heterocyclic ring, and $X^2$ is $CH_3$ or $C_2H_5$. 2,6-piperazinedione is similar to the heterocyclic amine expressed by Formula (3), but has a pKa of 4.3, and accordingly 2,6-piperazinedione is not practical as the heterocyclic amine according to the embodiment. 5-hydroxymethyl-1-methyl-2-piperazinone is similar to the heterocyclic amine expressed by Formula (4), but has a pKa of 6.6, and accordingly 5-hydroxymethyl-1-methyl-2-piperazinone is not practical as the heterocyclic amine according to embodiments.

More specific examples of the heterocyclic amines expressed by Formulas (3) and (4) may include at least one selected from the group consisting of; 2-piperazinone, 6-methyl-2-piperazinone, 1-methyl-2-piperazinone, 3-methyl-2-piperazinone, 5-methyl-2-piperazinone, 4-methyl-2-piperazinone, and the like.

It is practical that the organic solvent contained in the carbon dioxide absorbent according to embodiments has a boiling point of 150° C. or more at 1 atm. It has been found that since the organic solvent hardly volatilizes at the time of separating carbon dioxide when the organic solvent has a high boiling point, it is practical to use the organic solvent having a high boiling point, and in addition, it is possible to suppress an increase in viscosity of the carbon dioxide absorbent as compared to water at a high temperature at the time of separating carbon dioxide. When the viscosity of the carbon dioxide absorbent is increased at a high temperature, handling of the carbon dioxide absorbent may be difficult. Further, when the viscosity of the carbon dioxide absorbent is low at a high temperature, it is possible to efficiently separate carbon dioxide even though the temperature is low at the time of separating carbon dioxide, which is practical.

An example of the organic solvent having a boiling point of 150° C. or more at 1 atm may include an organic solvent having an amide bond or alcohols having 6 to 12 carbon atoms. A specific example of the organic solvent having a boiling point of 150° C. or more at 1 atm may include at least one selected from the group consisting of; dimethylacetamide, N-methyl pyrrolidone, dimethylformamide, diethyleneglycol dimethyl ether, dipropyleneglycol dimethylether, diethyleneglycol ethyl methyl ether, diethyleneglycol isopropyl methyl ether, diethyleneglycol diethyl ether, diethyleneglycol butyl methyl ether, tripropylene glycol dimethyl ether, triethylene glycol dimethyl ether, diethyleneglycol dibutyl ether, triethylene glycol butyl methyl ether, polyethylene glycol dimethyl ether, tetraethylene glycol dimethyl ether, hexanol, pentanol, octanol, nonanol, decanol, undecanol, dodecanol, and the like. In the case of alkyl carbonate based solvent, since a recovery amount of carbon dioxide is decreased due to a reaction with amine, the alkyl carbonate based solvent is not used.

Among the organic solvents having a boiling point of 150° C. or more at 1 atm, the organic solvent having an amide bond is more practically used. Among the organic solvents having a boiling point of 150° C. or more at 1 atm, in the case of the organic solvent having an amide bond, a recovery rate by separation of carbon dioxide is significantly high. An example of the organic solvent having a boiling point of 150° C. or more at 1 atm and having an amide bond may include at least one selected from the group consisting of; dimethylacetamide, N-methyl pyrrolidone, dimethylformamide, and the like. Besides, at least one alcohol selected from the group consisting of; hexanol, pentanol, octanol, nonanol, decanol, undecanol, dodecanol, and the like, may also be practically used.

Before absorbing carbon dioxide, in view of the recovery amount of carbon dioxide, it is practical that a total mass of the heterocyclic amine and the organic solvent is 70 mass % or more to 100 mass % or less of the carbon dioxide absorbent.

It is practical that a ratio of the heterocyclic amine to the organic solvent of the carbon dioxide absorbent ([a mass of the heterocyclic amine]/[a mass of the organic solvent]) is 1.5 or more to 9.0 or less. When the ratio of the heterocyclic amine to the organic solvent is less than 1.5, absorption/desorption capacity is decreased. When the ratio of the heterocyclic amine to the organic solvent is more than 9.0, an amine concentration of the heterocyclic amine is increased, and the viscosity at the time of absorbing carbon dioxide is increased, and accordingly, operability is deteriorated. The carbon dioxide absorbent according to embodiments may contain water in an amount equal to or less than mass % of the organic solvent. It is possible to suppress an increase in the viscosity at the time of absorbing carbon dioxide while maintaining a high recovery amount of carbon dioxide by adjusting the ratio in the above-mentioned range.

The viscosity of the carbon dioxide absorbent is measured by the VISCOMETER DV-II+Pro (made by Brookfield). In view of operability, it is practical that viscosity of an absorption solution is in a range of 0 mPa·s or more to 200 mPa·s or less, or a range of 72 mPa·s or more to 149 mPa·s or less at 25° C. regardless of an absorption amount of carbon dioxide. When the viscosity is increased after absorption of carbon dioxide, an amount of energy required to separate and recover carbon dioxide is increased, which is not practical in view of handling. The carbon dioxide absorbent according to embodiments is practical in that low viscosity is maintained before and after absorbing carbon dioxide.

Further, both before and after contacting the gas containing carbon dioxide with the carbon dioxide absorbent, a single phase state of the carbon dioxide absorbent according to embodiments is maintained. Even in the carbon dioxide absorbent which has absorbed carbon dioxide and thus has a saturated concentration of carbon dioxide, phase separation does not occur, and the single phase state is maintained. The carbon dioxide unabsorbed carbon dioxide absorbent is in a single phase state. The carbon dioxide absorbed carbon dioxide absorbent is in a single phase state. Since the phase separation does not occur, separation and recovery after absorbing carbon dioxide may be performed at a low temperature. Therefore, the carbon dioxide absorbent is significantly useful in view of handling and energy cost.

A quantitative and qualitative analysis method performed on total amines contained in the carbon dioxide absorbent is not particularly limited as long as the method can perform quantitative and qualitative analysis of amines. For example, the quantitative and qualitative analysis of total amines may be performed using high performance liquid chromatography (HPLC), liquid chromatography/mass spectrometry (LC/MS), liquid chromatography/tandem mass spectrometry (LC/MS/MS), liquid chromatography/time-of-flight mass spectrometry (LC/TOF-MS), gas chromatography/mass spectrometry (GC/MS), gas chromatography/tandem mass spectrometry (GC/MS/MS), gas chromatography/time-of-flight mass spectrometry (GC/TOF-MS), ion chromatography (IC), ion chromatography/mass chromatography (IC/MS), 1H nuclear magnetic resonance (1H-NMR), 13C magnetic resonance (13C-NMR), or the like.

The carbon dioxide absorbent may contain other components such as a deterioration inhibitor, an antifoaming agent, a viscosity modifier, and an antioxidant, in addition to the above-mentioned components. The carbon dioxide absorbent is not slurry but a solution.

<Method of Separating and Recovering Carbon Dioxide>

In a method of separating and recovering carbon dioxide according to embodiments, carbon dioxide is separated and recovered from gas containing carbon dioxide by contacting the gas containing carbon dioxide with a carbon dioxide unabsorbed carbon dioxide absorbent (the carbon dioxide absorbent according to embodiments) before absorbing carbon dioxide from the gas containing carbon dioxide according to the embodiment described above.

The method of separating and recovering carbon dioxide includes: (a) a process of absorbing carbon dioxide in the carbon dioxide unabsorbed carbon dioxide absorbent and obtaining a carbon dioxide absorbed carbon dioxide absorbent; and (b) a process of separating carbon dioxide from the carbon dioxide absorbed carbon dioxide absorbent which has absorbed carbon dioxide. In the process (a) of absorbing carbon dioxide, carbon dioxide is absorbed in the carbon dioxide unabsorbed carbon dioxide absorbent by contacting a carbon dioxide-containing exhaust gas with the carbon dioxide unabsorbed carbon dioxide absorbent. Further, in the process (b) of separating carbon dioxide, carbon dioxide is desorbed by heating the carbon dioxide absorbed carbon dioxide absorbent which has absorbed carbon dioxide obtained in the above-described process (a) of absorbing carbon dioxide. The desorbed carbon dioxide may be recovered, such that treatment such as storage, decomposition, or the like, of the carbon dioxide can be performed.

In the process (a) of absorbing carbon dioxide, a method of contacting the gas containing carbon dioxide with an aqueous solution containing the above-described carbon dioxide absorbent is not particularly limited. In the process (a) of absorbing carbon dioxide, for example, a method of bubbling the gas containing carbon dioxide in the carbon dioxide absorbent so as to be absorbed, a method of dropping the carbon dioxide absorbent in a mist form in a gas flow containing carbon dioxide (an atomizing or spraying method), a method of allowing the gas containing carbon dioxide and the carbon dioxide absorbent to come in countercurrent contact with each other in an absorption tower containing a filler made of a porcelain material or metal mesh, or the like, may be used.

In the process (a) of absorbing carbon dioxide, it is practical that at the time of absorbing the gas containing carbon dioxide in the aqueous solution, a temperature of the carbon dioxide absorbent is generally in a range of room temperature to 60° C. or less. The process of absorbing carbon dioxide is more practically performed at 50° C. or less, more specifically, about 20 to 45° C. The lower the temperature at which the process of absorbing carbon dioxide is performed, the larger the absorption amount of carbon dioxide, but a lower limit value of a treatment temperature is determined by a temperature of the gas, a heat recovery target, or the like in the process. Absorption of carbon dioxide is generally performed at approximately atmospheric pressure. Although it is possible to pressurize to a higher pressure to improve absorption performance, it is practical that absorption of carbon dioxide is performed at the atmospheric pressure to suppress energy consumption required for compression.

Here, a saturated absorption amount of carbon dioxide is a value obtained by measuring an amount of inorganic carbon in the carbon dioxide absorbent using an infrared (IR) type gas concentration meter. Further, an absorption rate of carbon dioxide is a value measured using an infrared type carbon dioxide meter after 2 minutes from the start of absorption of carbon dioxide.

In the process (b) of separating carbon dioxide, as a method of separating carbon dioxide from the carbon dioxide absorbent which has absorbed carbon dioxide and recovering pure or high-concentration carbon dioxide, a method of heating the carbon dioxide absorbent similarly to distillation and foaming in a kettle to desorb carbon dioxide, a method of heating the carbon dioxide absorbent in a plate tower, a spray tower, or a regeneration tower containing a filler made of a porcelain material or a metal mesh, while increasing a liquid interface, or the like, may be used. As a result, carbon dioxide is separated and released from carbamic acid anions or bicarbonate ions.

In the process (b) of separating carbon dioxide, a temperature of the carbon dioxide absorbent at the time of separating carbon dioxide is generally 70° C. or more. The temperature of the carbon dioxide absorbent at the time of separating carbon dioxide is practically 80° C. or more, and more practically about 90 to 120° C. The higher the temperature, the larger the absorption amount, but in the case of increasing the temperature, energy required to heat the absorption solution is increased. Therefore, the temperature of the carbon dioxide absorbent at the time of separating carbon dioxide is determined by the temperature of the gas, the heat recovery target, or the like in the process. It is practical that a pressure at the time of desorbing carbon dioxide is generally 0.1 to 0.5 MPa, and practically, about 0.1 to 0.2 MPa (absolute pressure).

The carbon dioxide absorbent after separating carbon dioxide is returned to and circulated and used (recycled) again in the process of absorbing carbon dioxide. Here, heat supplied at the time of release of carbon dioxide is generally heat-exchanged to thereby be cooled in a heat exchanger in order to pre-heat the carbon dioxide absorbent injected into the regeneration tower during a process of recycling the carbon dioxide absorbent.

Purity of the carbon dioxide recovered as described above is generally about 95 to 99 vol %, which is significantly high. This pure carbon dioxide or high-concentration carbon dioxide is used as a synthesis raw material of a chemical or a polymer material, a cooling agent for freezing food, or the like. In addition, the recovered carbon dioxide may also be separated and stored in a basement or the like, using methods being currently developed.

The largest energy is consumed in the process of separating carbon dioxide from the carbon dioxide absorbent to regenerate the carbon dioxide absorbent (the process of separating carbon dioxide) among the above-mentioned processes. In this process of separating carbon dioxide, about 50 to 80% of the energy in the entire process is consumed. Therefore, cost in the processes of absorbing and separating carbon dioxide can be decreased by reducing energy consumed in the process of separating carbon dioxide in which the carbon dioxide absorbent is regenerated. This makes it possible to economically advantageously perform the separation and recovery of carbon dioxide from the exhaust gas.

According to embodiments, energy required in the process of separating carbon dioxide (regeneration process) can be decreased by using the carbon dioxide absorbent according to embodiments. Therefore, the process of absorbing and separating carbon dioxide can be performed under economically advantageous conditions.

Further, an amine compound (1) according to embodiments described above has lower corrosivity toward metal materials such as carbon steel, as compared to alkanol amines such as monoethanol amine conventionally used as a carbon dioxide absorbent. Therefore, for example, the necessity to use a high-cost high-grade corrosion-resistant steel at the time of constructing a plant is decreased by adopting the method of separating and recovering carbon dioxide using the carbon dioxide absorbent according to embodiments, which is advantageous in view of cost.

<Apparatus of Separating and Recovering Carbon Dioxide>

An apparatus of separating and recovering carbon dioxide according to embodiments, the apparatus using the carbon dioxide absorbent of embodiments, the carbon dioxide absorbent being a carbon dioxide unabsorbed carbon dioxide absorbent, the apparatus includes: an absorption tower separating and recovering carbon dioxide from gas containing carbon dioxide by contacting the gas containing carbon dioxide the carbon dioxide unabsorbed carbon dioxide absorbent to allow carbon dioxide to be absorbed in the carbon dioxide unabsorbed carbon dioxide absorbent and a carbon dioxide absorbed carbon dioxide absorbent is obtained; and a regeneration tower configured to regenerate the carbon dioxide absorbed carbon dioxide absorbent by desorbing carbon dioxide from the carbon dioxide absorbed carbon dioxide absorbent which has absorbed carbon dioxide.

Figure 2:
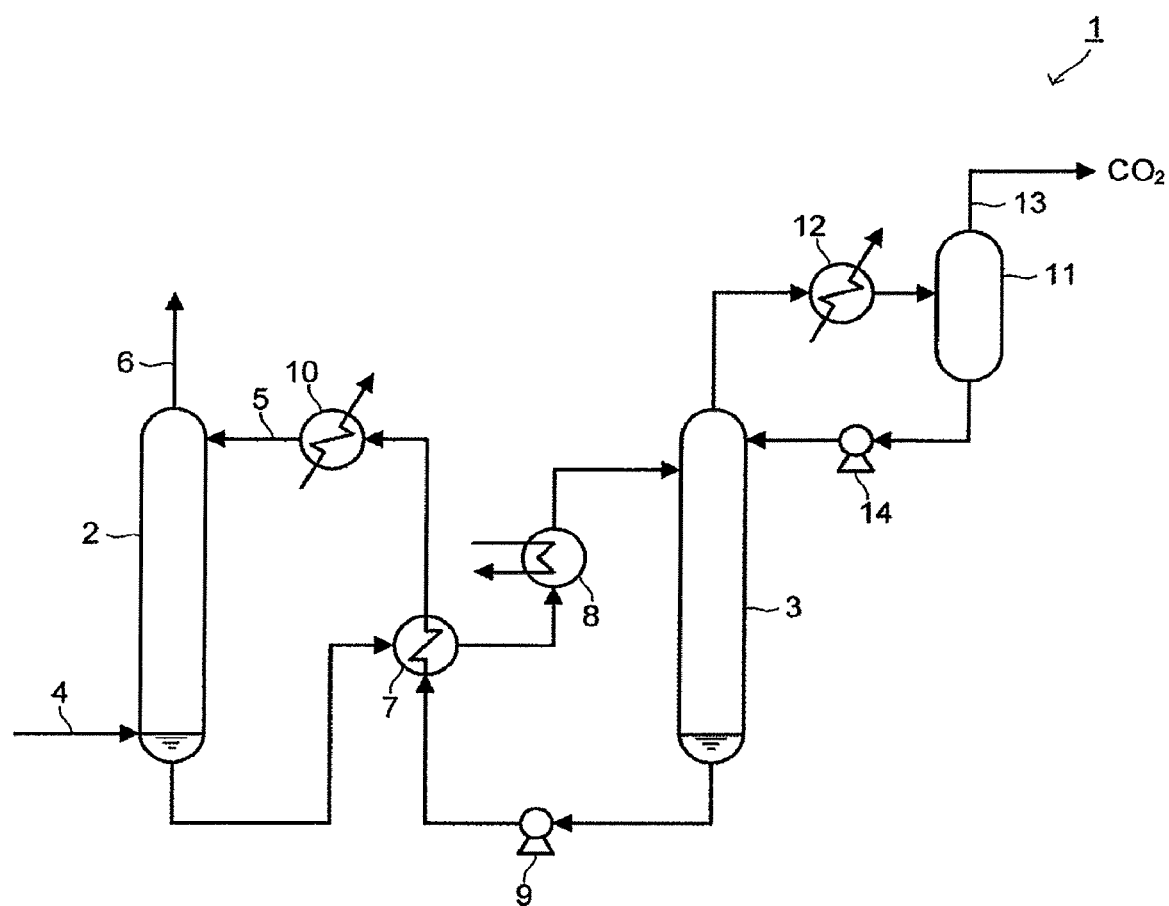
FIG. 2 is a schematic view of an apparatus of separating and recovering carbon dioxide according to embodiments.

FIG. 2 is a schematic view of the apparatus of separating and recovering carbon dioxide according to embodiments.

An apparatus 1 of separating and recovering carbon dioxide includes an absorption tower 2 and a regeneration tower 3. In the apparatus 1 of separating and recovering carbon dioxide, the absorption tower 2 separates and recovers carbon dioxide by contacting gas containing carbon dioxide (hereinafter, referred to as "exhaust gas") with a carbon dioxide absorbent and absorbing carbon dioxide from this exhaust gas. In the apparatus 1 of separating and recovering carbon dioxide, the regeneration tower 3 separates carbon dioxide from the carbon dioxide absorbent which has absorbed carbon dioxide in the absorption tower 2, and regenerates the carbon dioxide absorbent.

As illustrated in FIG. 2, the exhaust gas containing carbon dioxide such as combustion exhaust gas discharged from a thermal power plant, or the like, passes through a gas supply hole 4 to thereby be induced to a lower portion of the absorption tower 2. The carbon dioxide absorbent is supplied from a carbon dioxide absorbent supply hole 5 at an upper portion of the absorption tower 2 to thereby be accommodated in the absorption tower 2. The exhaust gas induced to the absorption tower 2 comes in contact with the carbon dioxide absorbent accommodated in the absorption tower 2. As the carbon dioxide absorbent, the carbon dioxide absorbent according to embodiments described above is used.

It is practical that a pH value of the carbon dioxide absorbent is adjusted to at least 9 or more. It is practical that an optimal pH value of the carbon dioxide absorbent is appropriately selected depending on the kind, a concentration, a flow rate, or the like of harmful gas contained in the exhaust gas. In addition, the carbon dioxide absorbent can contain other compounds such as a nitrogen-containing compound improving carbon dioxide absorption performance, an antioxidant, a pH adjuster, and the like, in an arbitrary ratio.

As described above, the exhaust gas comes in contact with the carbon dioxide absorbent in the absorption tower 2, such that carbon dioxide in the exhaust gas is absorbed in the carbon dioxide absorbent to thereby be separated and recovered from the exhaust gas. The exhaust gas after carbon dioxide is separated and recovered therefrom is discharged to the outside of the absorption tower 2 from a gas discharge hole 6.

The carbon dioxide absorbent which has absorbed carbon dioxide is sequentially transferred from the absorption tower 2 to a heat exchanger 7 and a heater 8 so as to be heated, and then transferred to the regeneration tower 3. The carbon dioxide absorbent transferred into the regeneration tower 3 is moved from an upper portion of the regeneration tower 3 to a lower portion thereof, and while the carbon dioxide absorbent is moved, carbon dioxide in the carbon dioxide absorbent is released, and the carbon dioxide absorbent is regenerated.

The carbon dioxide absorbent regenerated in the regeneration tower 3 is sequentially transferred to the heat exchanger 7 and an absorption solution cooler 10 by a pump 9, and is returned from the carbon dioxide absorbent supply hole 5 to the absorption tower 2.

Meanwhile, carbon dioxide separated from the carbon dioxide absorbent comes in contact with reflux water supplied from a reflux drum 11 in the upper portion of the regeneration tower 3 to thereby be discharged to the outside of the regeneration tower 3. The reflux water in which carbon dioxide is dissolved is cooled in a reflux condenser 12 and separated from a liquid component in which water vapor accompanied with carbon dioxide is condensed in the reflux drum 11. This liquid component is induced to the process of recovering carbon dioxide by a recovery carbon dioxide line 13. Meanwhile, the reflux water from which carbon dioxide is separated is transferred to the regeneration tower 3 by a reflux water pump 14.

With the apparatus 1 of separating and recovering carbon dioxide according to embodiments, it is possible to efficiently separate and recover carbon dioxide by using the carbon dioxide absorbent having excellent operability, absorption characteristics, and desorption characteristics of carbon dioxide.

Hereinafter, the carbon dioxide absorbent according to embodiments will be described in more detail through Examples.

Example 1

Bubbling of $CO_2$-containing gas was performed on a carbon dioxide absorbent in which 80 wt % of 1-ethoxycarbonylpiperazine and 20 wt % of N-methyl pyrrolidone were mixed with each other, and absorption equilibrium amounts of carbon dioxide at 40° C. to 70° C. were measured. A recovery amount of carbon dioxide was calculated from a difference between the measured absorption equilibrium amounts of carbon dioxide. Viscosity of a liquid in which $CO_2$ was bubbled at 40° C. was measured at 25° C. Further, presence or absence of phase separation was confirmed by naked eyes. The obtained results were summarized in Table 1.

Example 2

Bubbling of $CO_2$-containing gas was performed on a carbon dioxide absorbent in which 80 wt % of 1-ethoxycarbonylpiperazine and 20 wt % of dimethylacetamide were mixed with each other, and absorption equilibrium amounts at 40° C. to 70° C. of carbon dioxide were measured. Viscosity of a liquid in which $CO_2$ was bubbled at 40° C. was measured at 25° C. Further, presence or absence of phase separation was confirmed by naked eyes.

Example 3

Bubbling of $CO_2$-containing gas was performed on a carbon dioxide absorbent in which 80 wt % of 1-ethoxycarbonylpiperazine and 20 wt % of decanol were mixed with each other, and absorption equilibrium amounts of carbon dioxide at 40° C. to 70° C. were measured. Viscosity of a liquid in which $CO_2$ was bubbled at 40° C. was measured at 25° C. Further, presence or absence of phase separation was confirmed by naked eyes.

Example 4

Bubbling of $CO_2$-containing gas was performed on a carbon dioxide absorbent in which 80 wt % of 1-ethoxycarbonylpiperazine and 20 wt % of hexanol were mixed with each other, and absorption equilibrium amounts of carbon dioxide at 40° C. to 70° C. were measured. Viscosity of a liquid in which $CO_2$ was bubbled at 40° C. was measured at 25° C. Further, presence or absence of phase separation was confirmed by naked eyes.

Example 5

Bubbling of $CO_2$-containing gas was performed on a carbon dioxide absorbent in which 70 wt % of 1-Boc-piperazine and 20 wt % of dimethylacetamide were mixed with each other, and absorption equilibrium amounts of carbon dioxide at 40° C. to 70° C. were measured. Viscosity of a liquid in which $CO_2$ was bubbled at 40° C. was measured at 25° C. Further, presence or absence of phase separation was confirmed by naked eyes.

Example 6

Bubbling of $CO_2$-containing gas was performed on a carbon dioxide absorbent in which 70 wt % of 2-piperazinone and 30 wt % of dimethylacetamide were mixed with each other, and absorption equilibrium amounts of carbon dioxide at 40° C. to 70° C. were measured. Viscosity of a liquid in which $CO_2$ was bubbled at 40° C. was measured at 25° C. Further, presence or absence of phase separation was confirmed by naked eyes.

Example 7

Bubbling of $CO_2$-containing gas was performed on a carbon dioxide absorbent in which 80 wt % of 1-ethoxycarbonylpiperazine, 15 wt % of dimethylacetamide, and 5 wt % of water were mixed with each other, and absorption equilibrium amounts of carbon dioxide at 40° C. to 70° C. were measured. Viscosity of a liquid in which $CO_2$ was bubbled at 40° C. was measured at 25° C. Further, presence or absence of phase separation was confirmed by naked eyes.

Comparative Example 1

Bubbling of $CO_2$-containing gas was performed on a carbon dioxide absorbent in which 80 wt % of 1-ethoxycarbonylpiperazine and 20 wt % of water were mixed with each other, and absorption equilibrium amounts of carbon dioxide at 40° C. to 70° C. were measured. Viscosity of a liquid in which $CO_2$ was bubbled at 40° C. was measured at 25° C. Further, presence or absence of phase separation was confirmed by naked eyes.

Comparative Example 2

Bubbling of $CO_2$-containing gas was performed on a carbon dioxide absorbent in which 80 wt % of 1-ethoxycarbonylpiperazine and 20 wt % of ethylene glycol were mixed with each other, and absorption equilibrium amounts of carbon dioxide at 40° C. to 70° C. were measured. Viscosity of a liquid in which $CO_2$ was bubbled at 40° C. was measured at 25° C. Further, presence or absence of phase separation was confirmed by naked eyes.

TABLE 1

| | Recovery amount of carbon dioxide (40° C. to 70° C.) (NL/kg) | Viscosity (mPa · s) | Phase separation |
|---|---|---|---|
| Example 1 | 27 | 105 | Not occur |
| Example 2 | 29 | 72 | Not occur |
| Example 3 | 26 | 102 | Not occur |
| Example 4 | 27 | 149 | Not occur |
| Example 5 | 24 | 142 | Not occur |
| Example 6 | 26 | 130 | Not occur |
| Example 7 | 27 | 148 | Not occur |
| Comparative Example 1 | 28 | 217 | Not occur |
| Comparative Example 2 | 26 | 520 | Not occur |

From the results of Examples 1 to 7, while the recovery amount of $CO_2$ was maintained, an increase in viscosity at the time of loading $CO_2$ was suppressed by mixing a heterocyclic amine with a predetermined organic solvent with each other.

Here, some elements are expressed only by element symbols thereof.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A carbon dioxide absorbent comprising:
   a heterocyclic amine expressed by Formula (2), Formula (3), or Formula (4); and
   an organic solvent having a boiling point of 150° C. or more at 1 atm,
   wherein a total mass of the heterocyclic amine and the organic solvent is 70 mass % or more to 100 mass % or less of the carbon dioxide absorbent,
   $X^2$ in Formula (2) is CHO, $C(O)OC_2H_5$, $C(O)OC_3H_7$, $C(O)OCH(CH_3)_2$, $C(O)OC(CH_3)_3$, $C(O)OCH_3$, $C(O)CH_3$, or $C(O)C_2H_5$,
   $R^5$, $R^6$, and $R^7$ in Formula (3) are all H, or any one of $R^5$, $R^6$, and $R^7$ is $CH_3$ and the others are H, or
   $R^8$ in Formula (4) is oxygen double-bonded with carbon of the heterocyclic ring and $R^9$ is H; or $R^8$ is H and $R^9$ is oxygen double-bonded with carbon of the heterocyclic ring, and $X^3$ in Formula (4) is $CH_3$, and
   a mass ratio of the heterocyclic amine to the organic solvent is 1.5 or more to 9.0 or less Formula (2)

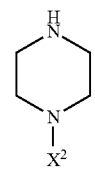

Formula (3)

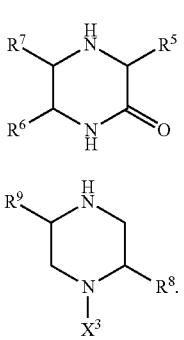

Formula (4)

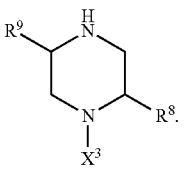

2. The absorbent according to claim 1, wherein the organic solvent is a solvent having an amide bond or an alcohol having 6 to 12 carbon atoms.

3. The absorbent according to claim 1, wherein the heterocyclic amine expressed by Formula (2) is at least one selected from the group consisting of 1-piperazinecarbaldehyde, 1-ethoxycarbonylpiperazine 1-n-propyloxycarbonylpiperazine, 1-i-propyloxycarbonylpiperazine, 1-piperazinecarboxylic acid-1-methylethyl ester, and 1-Boc-piperazine and the heterocyclic amine expressed by Formulas (3) and (4) is at least one selected from the group consisting of 2-piperazinone, 6-methyl-2-piperazinone, 1-methyl-2-piperazinone, 3-methyl-2-piperazinone, 5-methyl-2-piperazinone, and 4-methyl-2-piperazinone.

4. The absorbent according to claim 1, wherein the organic solvent is an alcohol having 6 to 12 carbon atoms.

5. The absorbent according to claim 1, wherein the organic solvent has an amide bond.

6. The absorbent according to claim 1, wherein the organic solvent is at least one selected from the group consisting of; dimethylacetamide, N-methyl pyrrolidone, and dimethylformamide.

7. The absorbent according to claim 1, wherein when carbon dioxide is dissolved at a saturation concentration in the carbon dioxide absorbent, the carbon dioxide absorbent is in a single phase state.

8. The absorbent according to claim 1, wherein viscosity of the carbon dioxide absorbent at 25° C. is 0 cps or more to 200 cps or less.

9. An apparatus of separating and recovering carbon dioxide, the apparatus comprising:
an absorption tower comprising the carbon dioxide absorbent according to claim 1 and configured to separate and recover carbon dioxide from gas containing carbon dioxide by contacting the gas containing carbon dioxide with the carbon dioxide absorbent in an unabsorbed state to allow carbon dioxide to be absorbed in the carbon dioxide absorbent and a carbon dioxide absorbed carbon dioxide absorbent is obtained; and
a regeneration tower configured to regenerate the carbon dioxide absorbent by desorbing carbon dioxide from the carbon dioxide absorbed carbon dioxide absorbent thus producing carbon dioxide and regenerated carbon dioxde absorbent.

10. The apparatus according to claim 9, wherein the organic solvent is an alcohol having 6 to 12 carbon atoms.

11. The apparatus according to claim 9, wherein the organic solvent has an amide bond.

12. The apparatus according to claim 9, wherein the organic solvent is at least one selected from the group consisting of; dimethylacetamide, N-methyl pyrrolidone, and dimethylformamide.

13. The apparatus according to claim 9, wherein when carbon dioxide is dissolved at a saturation concentration in the carbon dioxide absorbent, the carbon dioxide absorbent is in a single phase state.

14. The apparatus according to claim 9, wherein viscosity of the carbon dioxide absorbent at 25° C. is 0 cps or more to 200 cps or less.

15. The apparatus according to claim 9, wherein the organic solvent is a solvent having an amide bond or an alcohol having 6 to 12 carbon atoms.

16. The apparatus according to claim 9, wherein the heterocyclic amine expressed by Formula (2) is at least one selected from the group consisting of 1-piperazinecarbaldehyde, 1-ethoxycarbonylpiperazine, 1-n-propyloxycarbonylpiperazine, 1-i-propyloxycarbonylpiperazine, 1-piperazinecarboxylic acid-1-methylethyl ester, and 1-Boc-piperazine and the heterocyclic amine expressed by Formulas (3) and (4) is at least one selected from the group consisting of 2-piperazinone, 6-methyl-2-piperazinone, 1-methyl-2-piperazinone, 3-methyl-2-piperazinone, 5-methyl-2-piperazinone, and 4-methyl-2-piperazinone.

* * * * *